US00PP35388P2

(12) United States Plant Patent
Halladin

(10) Patent No.: US PP35,388 P2
(45) Date of Patent: Sep. 19, 2023

(54) ***THUJA* PLANT NAMED 'INGGSP'**

(50) Latin Name: ***Thuja plicata* x *standishii***
Varietal Denomination: INGGSP

(71) Applicant: Early Morning LLC, Boring, OR (US)

(72) Inventor: Paul H. Halladin, Boring, OR (US)

(73) Assignee: Early Morning, LLC, Boring, OR (US)

( * ) Notice: Subject to any disclaimer, the term of this patent is extended or adjusted under 35 U.S.C. 154(b) by 0 days.

(21) Appl. No.: 18/103,112

(22) Filed: Jan. 30, 2023

(51) Int. Cl.
*A01H 7/00* (2006.01)

(52) U.S. Cl.
USPC ..... Plt./213

(58) Field of Classification Search
USPC ..... Plt./213
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new *Thuja* plant particularly distinguished by having an extra narrow conical shape, one half of the growth rate of its parental line, a moderate garden size, uniform compact upright branching, small leaves, and foliage sprays arranged in a 3-dimensional curved pattern, is disclosed.

2 Drawing Sheets

Genus and species: *Thuja plicata* x *standishii*.
Variety denomination: 'INGGSP'.

BACKGROUND OF THE NEW PLANT

The present invention comprises a new and distinct variety of Hybrid Arborvitae, botanically known as *Thuja plicata* x *standishii* and hereinafter referred to by the variety name 'INGGSP'. 'INGGSP' is a selection discovered Dec. 26, 2018, in Boring, Oreg. as a three year old whole plant mutation in a commercial nursery of the commercial *Thuja* variety 'Green Giant' (unpatented). In December 2018, 'INGGSP' was first vegetatively propagated by rooted cuttings in Boring, Oreg. 'INGGSP' was found to reproduce true to type in successive generations of asexual propagation via semi hardwood rooted cuttings in Boring, Oreg.

SUMMARY

The following are the most outstanding and distinguishing characteristics of this new variety when grown under normal horticultural practices in Boring, Oreg.

1. 'INGGSP' is of moderate garden size.
2. 'INGGSP' exhibits one half the growth rate of its parent 'Green Giant'.
3. 'INGGSP' has an extra narrow conical shape.
4. 'INGGSP' displays uniform compact upright branching.
5. 'INGGSP' produces small leaves compared to its parent 'Green Giant'.
6. 'INGGSP' has foliage sprays arranged in a 3-dimensional curved pattern.

DESCRIPTION OF THE PHOTOGRAPHS

This new *Thuja* plant 'INGGSP' is illustrated by the accompanying photographs. The colors shown are as true as can be reasonably obtained by conventional photographic procedures.

Figure 1:
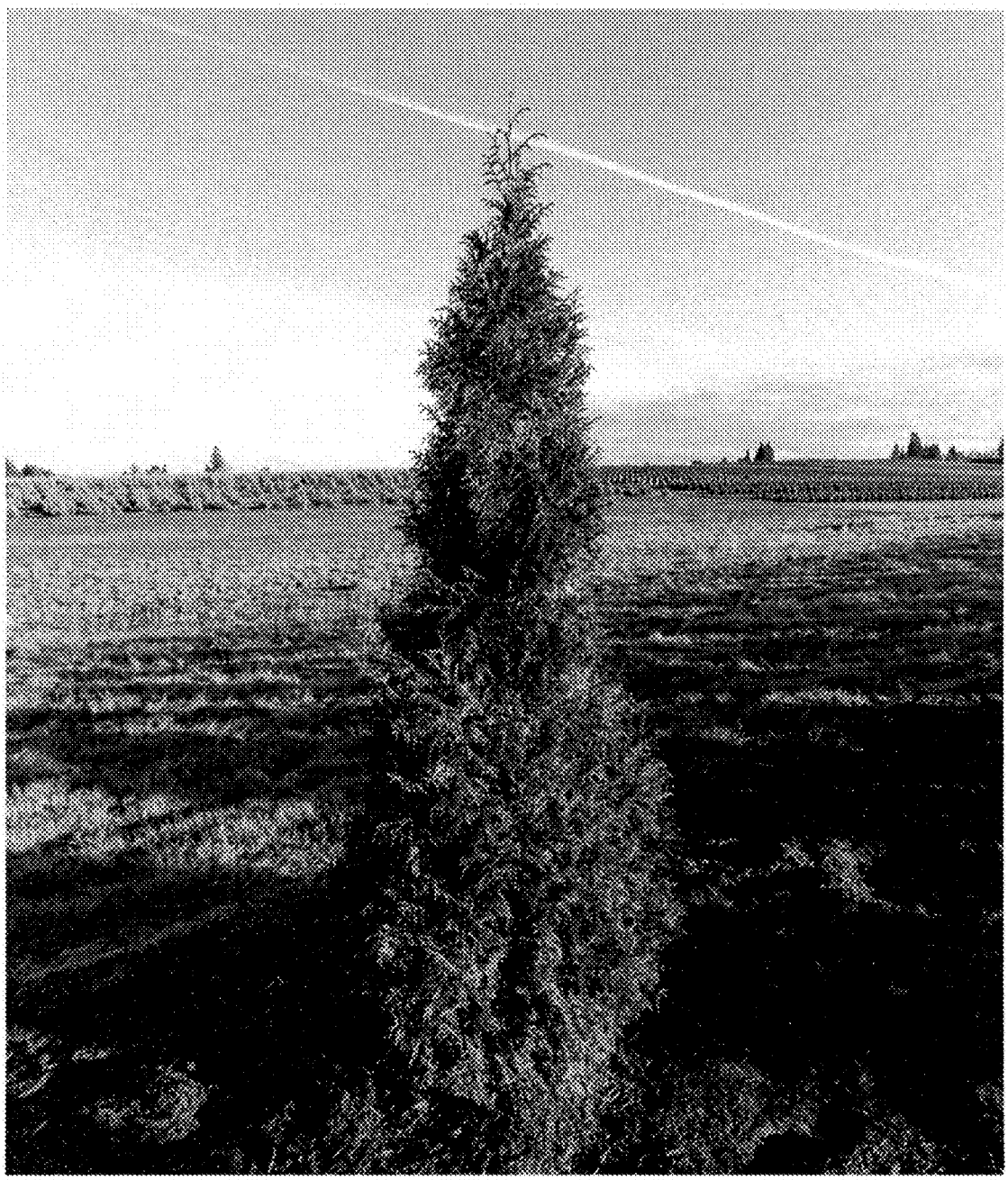

FIG. 1. is of a 'INGGSP' plant approximately seven-years-old, grown in the field in Boring, Oreg. in December 2022, which shows an overall habit and form of the plant.

Figure 2:
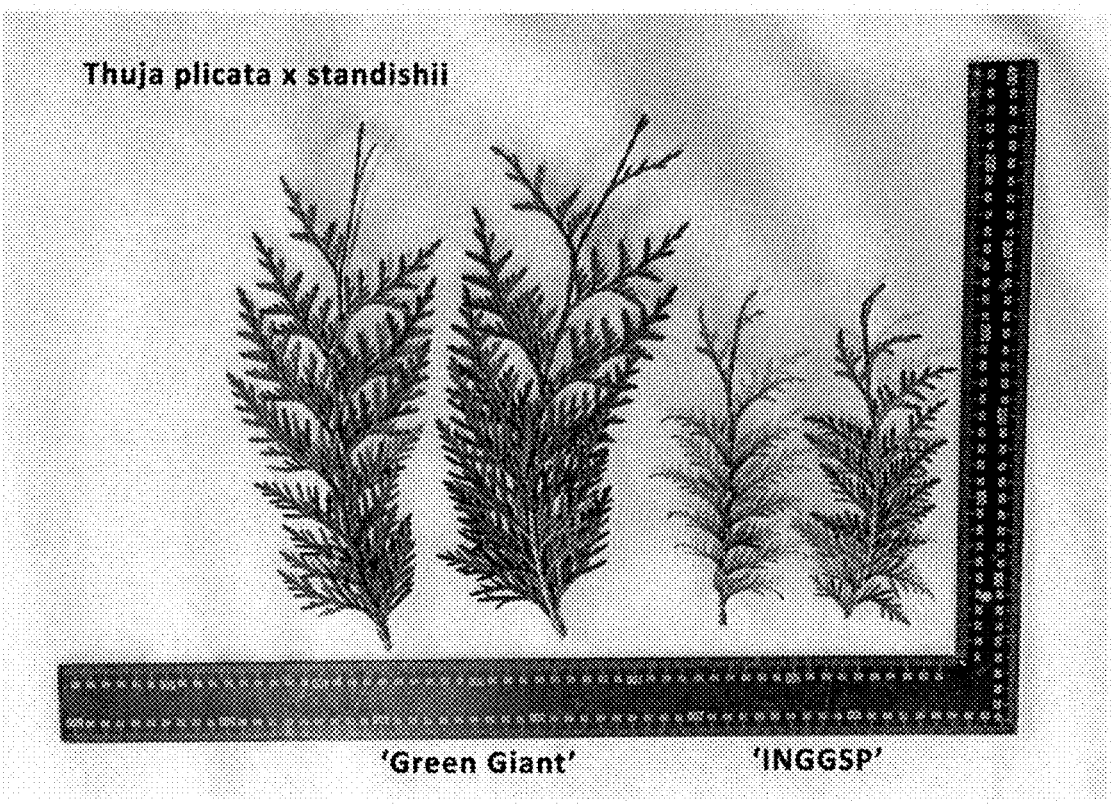

FIG. 2 illustrates the differences between foliage of the parental line 'Green Giant' and 'INGGSP'.

DESCRIPTION OF THE NEW VARIETY

The following detailed descriptions set forth the distinctive characteristics of 'INGGSP'. The data which define these characteristics were collected from asexual reproduction carried out in Boring, Oreg. Data was collected from a seven-year-old 'INGGSP' plant grown in the ground and four-year-old plants grown outdoors in containers in Boring, Oreg. in December of 2022. Color references are to The R.H.S. Colour Chart of The Royal Horticultural Society of London (R.H.S.), $4^{th}$ edition (2001).

Classification:
- *Family*.—Cupressaceae.
- *Species*.—*Thuja plicata* x *standishii*.
- *Common name*.—Hybrid Arborvitae.
- *Variety*.—'INGGSP'.

Parentage: *Thuja plicata* x *standishii* 'Green Giant' (unpatented).

Plant:
- *Form*.—Conical.
- *Growth habit*.—Extra narrow upright single trunk large tree, densely branched with foliage from base to crown.
- *Height*.—270.0 cm. at seven years.
- *Width*.—65.0 cm. at seven years.

Propagation:
- *Type cuttings*.—Semi hardwood rooted cuttings.
- *Time to produce rooted cutting*.—120 days.

Stem (trunk):
- *Diameter*.—8.0 cm at seven years (measured at 15.0 cm from soil).

*Texture*.—Two to four years: Smooth to slightly rough. Seven years: Vertical fissures with strips or flakes of fibrous bark.

*Color*.—Two to four years: RHS 166A. Seven years: RHS 198A fibrous strips with revealed RHS 183A smooth underlayment.

Lateral branches:

*Color*.—Young branch stems: RHS 174B. Mature branch stems: RHS 166A.

*Length*.—25.0 cm.

*Internode length*.—1.0 cm.

*Diameter*.—0.3 cm.

*Branching habit*.—Upward angled branches with single stem leader maintaining superiority with long branch shoots along the central trunk axis arranged in an alternate spiral pattern with a spacing of 3.0 cm to 6.0 cm.

*Texture*.—Smooth.

*Strength*.—Flexible.

Leaves:

*Arrangement*.—Scale-like leaves in alternate dissimilar pairs, flattened facial leaf pairs with triangular acute leaf tip in successive pairs separated by lateral leaf pairs with adpressed cuspidate leaf tip on new leaves with slightly spreading leaf tip with maturity.

*Fragrance*.—Sweet resinous aroma.

*Apex*.—Facial leaf: Acute. Lateral leaf: Cuspidate.

*Base*.—Truncate.

*Margin*.—Entire.

*Length*.—0.3 cm.

*Width*.—0.15 cm.

*Texture*.—Smooth, fleshy, and soft.

*Venation pattern*.—Inconspicuous.

*Color*.—Foliage: Upper surface: RHS 146A. Lower surface: RHS 157B wide stomatal zone separated by midrib RHS 146A.

*Leaf surface*.—Glabrous and glossy with a small to obscure resin gland on facial leaves.

*Aspect* (*arrangement on stem*).—Alternating opposite dissimilar pairs of facial and lateral leaves.

Flowering: No flowering observed.

Cone and seed set: Cone berry-like with no male or female cones or seeds observed.

Disease and insect resistance: No particular disease or insect resistance observed.

COMPARISON WITH PARENTAL LINE AND KNOWN VARIETY

'INGGSP' is distinguished from its mutation parent as described in Table 1:

TABLE 1

Comparison with Parental Line 'Green Giant'

| Trait or characteristic | New variety 'INGGSP' | Parent 'Green Giant' |
|---|---|---|
| Growth rate | 40.0 cm per season | 75.0 cm per season |
| Growth habit | Narrow upright | Broad upright |
| Branch spacing | Compact spacing 3.0 cm to 6.0 cm | Wide spacing 10.0 cm or more |
| 7-year size height by width | 270.0 cm high by 65.0 cm wide | 425.0 cm high by 215.0 cm wide |
| Leaf size length by width | 0.3 cm long by 0.15 cm wide | 0.6 cm long by 0.3 cm wide |

COMPARISON WITH SIMILAR VARIETY

'INGGSP' is most similar to the commercial *Thuja* plant named 'Hogan' (unpatented). Differences between the two varieties are described in Table 2:

TABLE 2

| Trait | Variety 'INGGSP' | Commercial line 'Hogan' |
|---|---|---|
| Growth rate | 40.0 cm per season | 60.0 cm per season |
| Branchlets | 3-dimentional curved shoot and leaf spray arrangement | Flat linear leaf sprays |

I claim:

1. A new and distinct variety of *Thuja* plant named 'INGGSP' as shown and described herein.

* * * * *